United States Patent
Saini et al.

(10) Patent No.: US 12,011,252 B2
(45) Date of Patent: Jun. 18, 2024

(54) SENSORS FOR IN-VIVO MEASUREMENTS

(71) Applicant: Teliatry, Inc., Richardson, TX (US)

(72) Inventors: Rahul Saini, Allen, TX (US); Dane William Grasse, Santa Clara, CA (US); Vishnoukumaar Sivaji, Richardson, TX (US)

(73) Assignee: Teliatry, Inc., Richardson, TX (US)

( * ) Notice: Subject to any disclaimer, the term of this patent is extended or adjusted under 35 U.S.C. 154(b) by 214 days.

(21) Appl. No.: 17/233,776

(22) Filed: Apr. 19, 2021

(65) Prior Publication Data

US 2022/0330843 A1 Oct. 20, 2022

(51) Int. Cl.
*A61B 5/0215* (2006.01)
*A61B 5/00* (2006.01)
(Continued)

(52) U.S. Cl.
CPC ........ *A61B 5/02158* (2013.01); *A61B 5/0031* (2013.01); *A61B 5/0538* (2013.01); *A61B 5/076* (2013.01); *A61B 5/14539* (2013.01); *A61B 5/1473* (2013.01); *A61B 5/6861* (2013.01); *A61B 5/6898* (2013.01); *A61B 6/425* (2013.01); *A61B 8/12* (2013.01); *H02J 50/20* (2016.02); *A61B 2560/0214* (2013.01); *A61B 2562/0233* (2013.01); *A61B 2562/0247* (2013.01);
(Continued)

(58) Field of Classification Search
None
See application file for complete search history.

(56) References Cited

U.S. PATENT DOCUMENTS 4,023,562 A * 5/1977 Hynecek ............. G01L 19/0061
338/42
4,691,709 A * 9/1987 Cohen .................. A61B 5/0261
73/705
(Continued)

FOREIGN PATENT DOCUMENTS

WO 2004014456 A2 2/2004
WO 2006122750 A1 11/2006
WO WO-2021186009 A1 * 9/2021 ......... A61B 5/02156

OTHER PUBLICATIONS

Brancato, Luigi et al. "An Implantable Intravascular Pressure Sensor for a Ventricular Assist Device," MicroMachines, 2016, 17 pages.
(Continued)

*Primary Examiner* — Devin B Henson
*Assistant Examiner* — Matthew Eric Ogles
(74) *Attorney, Agent, or Firm* — Slater Matsil, LLP (57) ABSTRACT

In one embodiment, a sensor includes a capsule having a cavity and a sheath, a transducer coupled to electronic circuitry in the cavity, and a clip outside the capsule. The capsule and the clip are configured to hold in vivo an object within an opening between the capsule and the clip. The transducer is configured to detect an incoming signal indicative of a physiological parameter of the object being held, and the electronic circuitry is configured to wirelessly transmit a signal containing information about the physiological parameter obtained from the incoming signal. The sensor is part of a measurement system to measure the physiological parameter. Another embodiment describes a method using the measurement system.

19 Claims, 4 Drawing Sheets

(51) Int. Cl.
*A61B 5/0538* (2021.01)
*A61B 5/07* (2006.01)
*A61B 5/145* (2006.01)
*A61B 5/1473* (2006.01)
*A61B 6/42* (2024.01)
*A61B 8/12* (2006.01)
*H02J 50/20* (2016.01)

(52) U.S. Cl.
CPC .............. *A61B 2562/0261* (2013.01); *A61B 2562/0271* (2013.01); *A61B 2562/164* (2013.01)

(56) References Cited

U.S. PATENT DOCUMENTS

| | | | | |
|---|---|---|---|---|
| 5,564,434 | A | * | 10/1996 | Halperin .............. A61N 1/3655 600/561 |
| 6,106,477 | A | * | 8/2000 | Miesel ................. A61B 5/6884 623/1.1 |
| 6,855,115 | B2 | | 2/2005 | Fonseca et al. |
| 8,602,999 | B2 | | 12/2013 | Young et al. |
| 11,000,195 | B2 | * | 5/2021 | Joseph ................. A61B 5/6876 |
| 2007/0038255 | A1 | * | 2/2007 | Kieval ............... A61N 1/36135 607/4 |
| 2011/0066046 | A1 | * | 3/2011 | Young ................ A61B 5/02241 600/486 |

OTHER PUBLICATIONS

Cong, Peng et al., "Wireless Batteryless Implantable Blood Pressure Monitoring Microsystem for Small Laboratory Animals," IEEE Sensors Journal, vol. 10, No. 2, Feb. 2010, 12 pages.

Honjol, Yazan, et al., "Current view and prospect: Implantable pressure sensors for health and surgical care," Wiley Periodicals, Inc., Feb. 9, 2020, 18 pages.

Hu, Shiyan et al., "A wireless passive extra-arterial implantable blood pressure monitoring sensing system for rats," Microsystem Technologies, Aug. 27, 2020, 9 pages.

Yacoub, Magdi H., et al., "The expanding role of implantable devices to monitor heart failure and pulmonary hypertension," Nature, Dec. 2018, vol. 15, 2018, 10 pages.

* cited by examiner

SENSORS FOR IN-VIVO MEASUREMENTS

GOVERNMENT LICENSE RIGHTS

This invention was made with government support under a contract (UC Davis Contract #N66001-20-2-4046/Sub Contract A21-0795-5003) awarded by Defense Advanced Research Projects Agency (DARPA). The government has certain rights in the invention.

TECHNICAL FIELD

The present invention relates generally to a system and method for measurements, and, in particular embodiments, to systems, devices, and methods for in vivo measurements.

BACKGROUND

Readings of physiological parameters such as pulse, temperature, blood pressure, and blood chemistry are important for medical diagnosis and treatment. However, monitoring of pertinent parameters is typically infrequent, with roughly a few measurements a year during clinic visits. Indeed, the difficulty in acquiring, analyzing, and delivering patient data for health screening is a barrier to expansion of preventive medicine. The conventional measurement systems are often restrictive for the patient, which hinders tracking of physiological parameters. Fluid pressures in many internal systems and organs are recognized to be predictors or indicators of organ health. Blood pressure (BP), intraocular pressure (TOP), and intracranial pressure (ICP) are examples of clinically relevant pressure readings used to diagnose or predict diseases of the heart, kidney, eye, or brain. Hypertension or high average BP, averaged over a week, for example, is understood to damage organs such as the heart and kidneys, and is usually treated with medication. Diagnosing hypertension and evaluating medications need accurate measurement of the long-term average BP. A good estimate of the true average BP may require collecting over ten readings during several weeks to compile a reasonable sample size. Transient BP changes are difficult to measure, but may indicate medical conditions such as baroreceptor dysfunction. Transient BP changes such as orthostatic hypotension may manifest in conditions like multiple sclerosis, Parkinson's disease, and spinal cord injury; hence a mean arterial blood pressure (MAP), monitored with an in-vivo MAP sensor may provide useful information for patient therapy. A MAP can also be a biomarker used to examine the effect of acute spinal cord injury on hemodynamic parameters in humans. Innovative in vivo BP measurement systems are needed to address these issues.

SUMMARY

A sensor including: a clip including an inner surface; a capsule including a cavity and a sheath enclosing the cavity, the sheath including a first portion attached to the inner surface and a second portion, the capsule and the clip being configured to hold in vivo an object within an opening between the second portion of the capsule and the inner surface of the clip; a transducer disposed in the cavity, the transducer being configured to detect in vivo an incoming signal received via the second portion, the incoming signal indicative of a physiological parameter of the object inside a living organism; and electronic circuitry disposed in the cavity and coupled to the transducer, where the electronic circuitry includes a wireless system, the wireless system including a power supply system, the power supply system configured to receive power wirelessly from an external radio frequency (RF) power source and supply power to operate the electronic circuitry, the external RF power source configured to be outside the living organism, and where the electronic circuitry is configured to transmit a signal containing information about the physiological parameter obtained from the incoming signal.

A measurement system including: a sensor configured to be attached within a living organism, the sensor including: a capsule including a cavity and a sheath enclosing the cavity, the sheath including a first portion and a second portion; a clip disposed outside the capsule, the clip being configured to attach to the first portion and to hold in vivo an object between the second portion and the clip; a transducer disposed in the cavity, the transducer being configured to detect in vivo an incoming signal received via the second portion, the incoming signal indicative of a physiological parameter of the object; and electronic circuitry disposed in the cavity and coupled to the transducer, where the electronic circuitry includes a first wireless system, the first wireless system including a power supply system configured to receive power wirelessly from an external radio frequency (RF) power source and supply power to operate the electronic circuitry, the external RF power source configured to be outside the living organism, and where the electronic circuitry is configured to transmit a signal containing information about the physiological parameter obtained from the incoming signal; and an electronic system configured to be outside the living organism, the electronic system including: a second wireless system, the second wireless system being configured to communicate wirelessly with the first wireless system; and a computer system.

A measurement method, where the method provides a measure of a physiological parameter of an object inside a living organism, the method including: implanting a sensor inside the living organism, the sensor including: a capsule including a cavity and a sheath enclosing the cavity, the sheath including a first portion and a second portion; a clip disposed outside the capsule; a transducer disposed in the cavity, the transducer being configured to detect an incoming signal from the object received via the second portion; and electronic circuitry disposed in the cavity and coupled to the transducer, the electronic circuitry including a first wireless system; configuring the clip to attach to the first portion and to hold in vivo the object between the second portion and the clip; converting the incoming signal in vivo to a first output signal with the transducer, the first output signal being an electrical signal indicative of the physiological parameter of the biological sample; generating a second output signal from the first output signal with the electronic circuitry, the second output signal containing information about the physiological parameter; transmitting the second output signal wirelessly to an electronic system disposed outside the living organism with the first wireless system; and obtaining a measure of the physiological parameter from the second output signal with the electronic system.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF ILLUSTRATIVE EMBODIMENTS

Various embodiments leverage advances in electronic sensors and wireless technology. Medical implants comprising sensors and electronic circuitry enable mobile health systems, which may provide frequent and even ambulatory monitoring using a wireless network of mobile devices.

This disclosure describes measurement systems and methods for measuring in vivo a physiological parameter of an object such as a tissue in a living organism. The measurements are done using an implantable sensor attached to the object and an electronic system outside the body in wireless communication with the sensor.

Figure 1A:
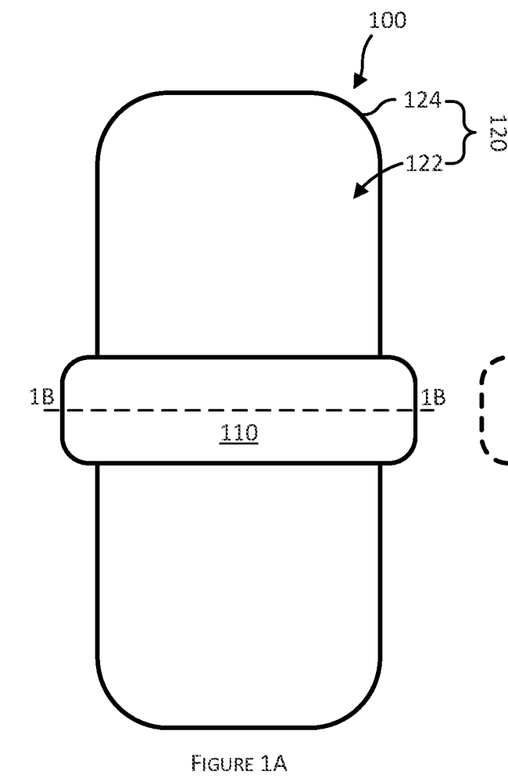
FIG. 1A illustrates a schematic of a sensor, in accordance with an embodiment.

FIG. 1A illustrates a schematic of an example embodiment of a sensor 100. The sensor 100 comprises a clip no and a capsule 120 comprising a cavity 122 enclosed by a sheath 124. The clip no is disposed outside the capsule 120.

Figure 1B:
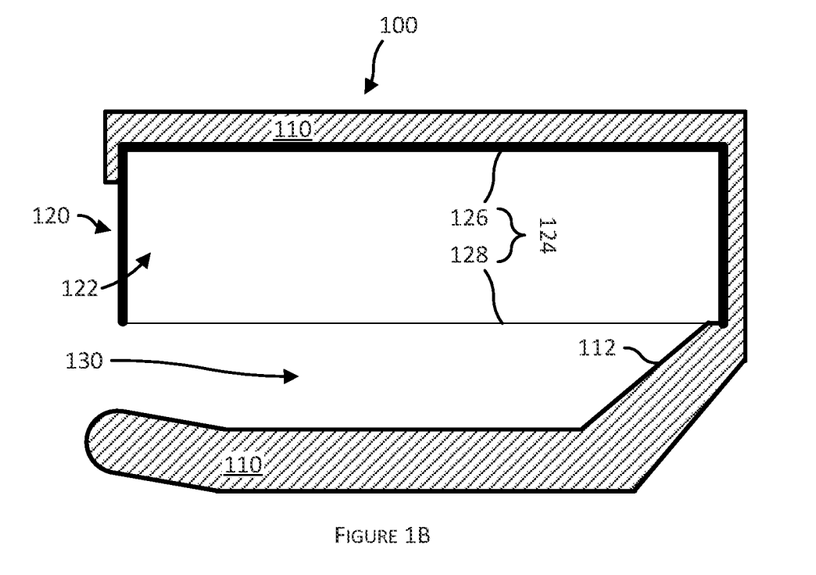
FIG. 1B illustrates a cross-sectional view of the sensor illustrated in FIG. 1A.

A cross-sectional view of the sensor 100 illustrated in FIG. 1B shows a first portion 126 of the sheath 124 attached to an inner surface 112 of the clip 110, and an opening 130 between a second portion 128 of the sheath 124 and the inner surface 112 of the clip 110. In the embodiments described in this disclosure, the capsule 120 and the clip no are configured to physically hold the object of interest within the opening 130. For example, the dimensions of the various parts of the sensor 100 may be designed to hold an artery of the living organism in the opening 130 between the inner surface 112 of the clip no and the second portion 128 of the sheath 124.

The clip no may comprise a rigid material such as polytetrafluoroethylene (PTFE or Teflon) which is a synthetic fluoropolymer of tetrafluoroethylene suitable for implanting inside the body of a living organism (e.g., subcutaneous tissue in a human arm). The sheath 124 may comprise glass that is suitable to be implanted in a living organism. Glasses suitable to be implanted include Corning HPSF 7979, 7980, 8655 Fused Silica, Schott Borofloat 33, MEMpax, AF32 eco, D263 family of glass.

In some embodiments, the material used for the first portion 126 may be rigid and the second portion 128 may be flexible. The second portion 128 could be made flexible by using a thin material, for example, by thinning the glass in the second portion 128. In other words, the first portion 126 and the second portion 128 may comprise the same material except that the thickness of the second portion 128 is less than the thickness of the first portion 126, as indicated by the relatively thick outline used to draw the first portion 126 in FIG. 1B. In one or more embodiments, the first portion 126 is about two to ten times thicker than the second portion 128. Specifically, the second portion 128 is made to be thin enough to be flexible.

Figure 1C:
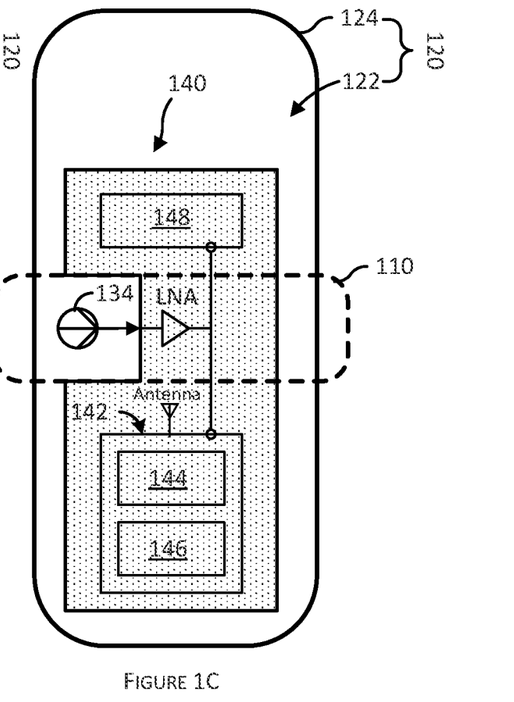
FIG. 1C illustrates a schematic of components in a cavity of a capsule of the sensor illustrated in FIG. 1A.

FIG. 1C is a schematic diagram of the capsule 120 showing the components inside the cavity 122 in a block diagram. The clip no is indicated by a dashed line in FIG. 1C.

As illustrated in FIG. 1C, electronic circuitry 140 and a transducer 134 may be placed inside the cavity 122 of the capsule 120, and coupled to each other. The transducer 134 is configured to detect a signal originating from the object of interest, indicative of its physiological parameter. Generally, the transducer 134 would be placed adjacent to the second portion 128 of the sheath 124 (see FIG. 1B) to better intercept the incoming signal originating from the object of interest held within the opening 130. The clip no may be adjusted in vivo to orient the sensor 100 such that the incoming signal may easily couple to the transducer 134 via the second portion 128 of the sheath 124. The transducer 134 generates a first output signal by converting the incoming signal to an electrical signal. In some embodiments, the transducer 134 may comprise a variable electronic component (e.g., a variable capacitor or resistor) whose variation indicates a respective variation in the physiological parameter. In these embodiments, the transducer 134 is often connected in an electrical circuit included in the electronic circuitry 140. The electrical circuit may be configured such that an electrical signal of the circuit gets modulated by the variation of the variable electronic component, thereby generating an electrical signal indicative of the variation of the physiological parameter.

The electrical first output signal is provided to the electronic circuitry 140, as indicated by an arrow in FIG. 1C. For example, in embodiments of measurement systems suitable for measuring fluid pressure in an object held by the sensor 100 in the opening 130, the second portion 128 of the sheath 124 may comprise a flexible material whose shape responds to a change in the fluid pressure. The incoming signal may be a time-varying displacement of the flexible second portion 128 indicative of, for example, blood pressure (BP) of a pulsating artery held by the sensor 100, and the transducer 134 may be a pressure transducer. In various embodiments where the sensor 100 is a pressure sensor, the transducer 134 may be using various techniques to convert the time-varying displacement to a time-varying electrical first output signal indicative of pressure (e.g., the arterial BP), as described in further detail below.

In the example embodiments described in this disclosure, the transducer 134 is a pressure transducer, and the applications is measurement of extravascular arterial BP. In other embodiments the transducer 134 may be a pressure transducer used to detect intracranial, intraocular, orthopedic, and bladder pressure.

In various embodiments, the transducer 134 may detect pressure using various physical phenomena. A pressure transducer may be, for example, a strain gauge, a piezoelectric device, a piezoresistive device, a variable capacitive device, a variable inductive device, a quantum tunneling device, or an optical device such as a deformable mirror, a deformable diffraction grating, and an interferometer.

In various other embodiments, the transducer 134 may be a chemical sensor device, a pH sensor device, a thermometer, a thermoelectric device, an ultrasound detector, a Hall Effect sensor, an electric potential detector, an x-ray detector, a photodetector, or a radioactive radiation detector.

As described above, the transducer 134 is generally sealed from the opening 130 by the second portion 128 of the sheath 124. In some embodiments, the transducer 134 may have an outer surface that is part of the second portion 128 of the sheath 124. A configuration where part of the second portion 128 is also a portion of the transducer 134 may be used is to sense in-vivo a chemical property (e.g., pH) of a fluid. For example, in one embodiment, the transducer 134 may be a metal oxide semiconductor field effect transistor (MOSFET) pH sensor device, and an outer surface of the transducer 134 comprising the gate may be part of the second portion 128 of the sheath 124 electrically coupled to the MOSFET.

The electronic circuitry 140 is configured to receive the first output signal from the transducer 134, generate a second output signal from the first output signal, and wirelessly transmit the second output signal to receivers outside the body. The second output signal contains information from which a measure of the physiological parameter of the tissue of interest may be obtained, as described further below. In some embodiments, the first output signal received from the transducer 134 may be amplified by a low-noise amplifier (LNA) included in the electronic circuitry 140, as illustrated in FIG. 1C.

Still referring to FIG. 1C, the electronic circuitry 140 comprises a first wireless system 142 and, in some embodiment, comprises additional signal processing circuitry 148. The first wireless system 142 comprises electronic communications circuitry 144 used in wireless communications systems, such as a radio frequency (RF) oscillator and RF modulator. As illustrated in FIG. 1C, the first wireless system 142 further comprises a power supply 146, which may be configured to supply DC power using RF power received from an RF source outside the body. The additional signal processing circuitry 148 may optionally process the first output signal using circuitry configured to perform signal processing functions such as low-pass filtering, analog to digital (A/D) conversion, and digital encoding that may be optionally included in the electronic circuitry 140 of the sensor 100.

In some embodiments where the electronic circuitry 140 comprises additional signal processing circuitry 148, signal processing techniques may be applied to the first output signal (or the amplified first output signal) to enhance the quality of the communication between the sensor 100 and electronics systems outside the body. For example, in one embodiment, a low-pass filter or a bandpass filter may be used to improve the signal to noise ratio (SNR) of the first output signal. In another embodiment, the first output signal may be sampled with a sample-and-hold circuit, discretized, and digitized by an A/D converter. The digital signal may be provided to a digital signal processor for signal processing, such as encoded by a digital encoder using various coding techniques, for example, pseudo random noise (PRN) codes for a spread spectrum system. The spread spectrum technique comprises spreading the signal power of the coded signal intentionally over a wider spectrum. Techniques such as the spread spectrum technique help increase the noise immunity of a weak signal transmitted through a noisy channel, thereby conserving RF power consumed in the wireless transmission of the second output signal.

The second output signal is generated from the first output signal (optionally processed by the additional signal processing circuitry 148) for wireless transmission by the first wireless system 142. For example, an RF oscillator of the electronic communications circuitry 144 may generate an RF carrier signal. The first output signal, optionally processed, may modulate the RF carrier signal in an RF modulator circuit of the electronic communications circuitry 144, thereby generating a modulated RF signal containing information about the physiological parameter. The modulated RF signal may be the second output signal that is transmitted wirelessly to receivers outside the body using an antenna of the first wireless system 142 in the cavity 122 of the capsule 120, as illustrated in FIG. 1C.

The power supply 146 may be configured to receive RF power from an RF source outside the body. In some embodiments, the antenna used for transmitting the second output signal may be used by the power supply 146 to receive RF power while, in some other embodiments, the power supply 146 may have a separate antenna. The received RF signal may be converted to DC power and coupled to a power supply network to distribute DC power to operate various components of the electronic circuitry 140. The conversion from RF power to DC power may be achieved by the power supply 146 using, for example, rectifiers and voltage regulators. In some embodiments, the power supply 146 may include a rechargeable battery to operate the components of the electronic circuitry 140. The external RF power may then be used by the power supply 146 to charge the rechargeable battery.

Without a rechargeable battery, the electronic circuitry 140 in the sensor 100 may not be able to communicate data wirelessly to an external receiver during a period when there is no external power source providing power wirelessly to the power supply 146. This constraint is removed in embodiments with a rechargeable battery; wireless communication with an external receiver may be optionally done at all times. For example, the measured data may be stored within an internal memory and then periodically transmitted to external receivers, transmitted upon demand, or upon determining of an emergency.

In various embodiments, the electronic circuitry 140 may comprise programmable components. A programmable component may comprise a one-time programmable (OTP) device (e.g., an OTP memory or field-programmable gate array (FPGA)) or a re-programmable device (e.g., a digital signal processor or a microcontroller).

Figure 2A:
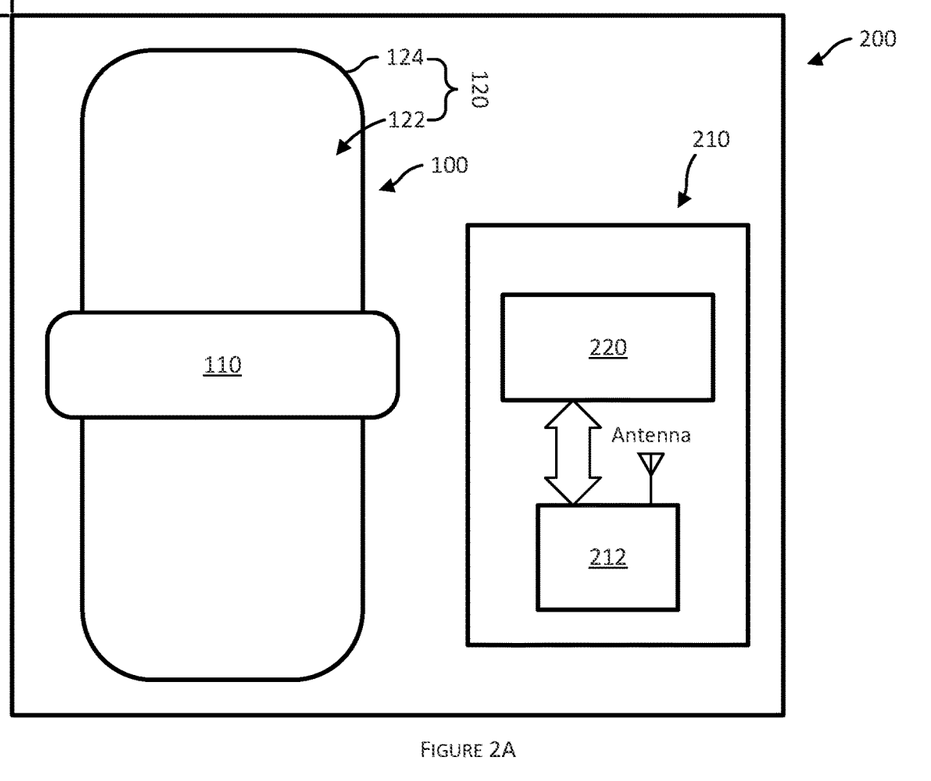
FIG. 2A illustrates a schematic of a measurement system in accordance with an embodiment.

FIG. 2A illustrates a schematic of a measurement system 200 comprising the sensor 100 (e.g., described in FIGS. 1A-1C) and the electronic system 210 configured to be outside the body of the living organism.

The sensor 100 configured to be inside the body and the electronic system 210 configured to be outside the body may communicate via a short range wireless communication channel using, for example, near field communication (NFC) or Bluetooth protocols such as Bluetooth Low Energy. The electronic system 210 comprises a second wireless system 212 and a computer system 220 coupled to each other via a data communication channel, as indicated by a double-arrow in FIG. 2A.

As indicated by an antenna in FIG. 2A, the second wireless system 212 comprising an RF receiver and associated signal processing circuitry is configured to receive the second output signal transmitted wirelessly from inside the body by the first wireless system 142 (see FIG. 1C) of the sensor 100. The second wireless system 212 may also include a transmitter (or a transceiver) to both receive and transmit communications. In some embodiments, the transmitter may be an RF transmitter configured to wirelessly transmit an RF signal.

As mentioned above, the second output signal received from the sensor 100 contains information indicative of the physiological parameter. Signal processing circuitry in the second wireless system 212 such as a demodulator, decoder, modulator, encoder, and the like may be configured to generate a third output signal from the second output signal. The third output signal includes the information about the physiological parameter contained in the received second output signal. Generally, the signal processing is done using digital signal processing techniques, and the information is coded in a digital format in the third output signal before communicating it to the computer system 220 via the data communication channel indicated by a double-arrow in FIG. 2A.

As mentioned above, the data communication channel couples the second wireless system 212 and the computer system 220 of the electronic system 210 outside the body. The coupling may be either a wireless connection between separate devices or a wired connection in an integrated device. In some embodiments, the second wireless system 212 may be in a mobile device (e.g., a laptop computer or a smart phone). In one embodiment, the mobile device may be configured to be wearable by the living organism in which the sensor 100 may be implanted. For example, the second wireless system 212 may be in a wristband, worn similar to a wristwatch. In some embodiment, the second wireless system 212 (e.g., in the wristband) and the computer system 220 may communicate data using NFC or Bluetooth technology.

In some embodiments, the second wireless system 212 may comprise an RF transmitter configured to transmit information to the first wireless system 142 of the sensor 100, for example, to remotely adjust programmable components in the electronic circuitry 140 (see FIG. 1C) of the sensor 100. In addition, the second wireless system 212 may supply RF power from outside the body to the power supply 146 (see FIG. 1C) inside the cavity 122 of the sensor wo, although it is understood that a separate RF source may be used in some embodiments as the external source of RF power used by the sensor 100.

Figure 2B:
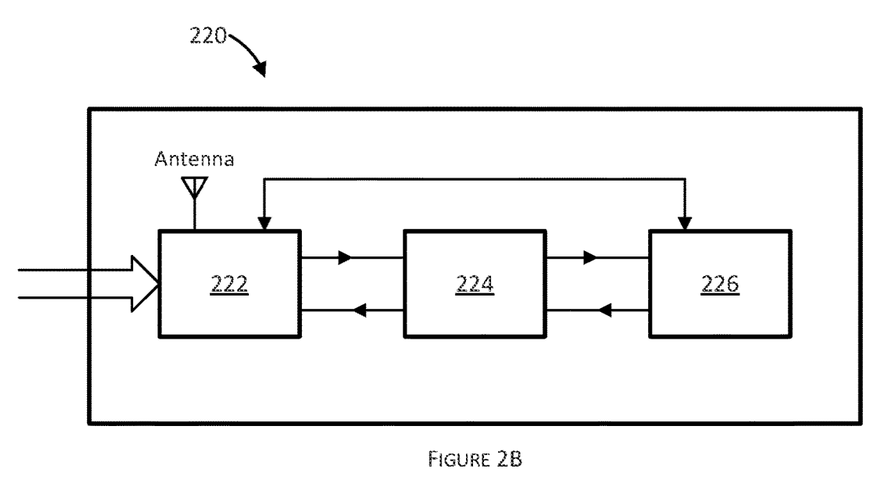
FIG. 2B illustrates a block diagram of the computer system of the measurement system illustrated in FIG. 2A.

FIG. 2B illustrates a block diagram of the computer system 220. The computer system 220 comprises a data communication system 222, a processor 224, and a memory 226.

The data communication system 222 is configured to communicate with the second wireless system 212 via the data communication channel, indicated by an open-arrow in FIG. 2B. The data communication system 222 receives the third output signal containing information about the physiological parameter communicated by the second wireless system 212. Signal processing techniques may be applied to extract the information using circuitry included in the data communication system 222. The extracted information may be directly provided to the processor 224 and/or stored in memory 226, as indicated by connecting arrows in the schematic illustrated in FIG. 2B.

In addition, the data communication system 222 may be communicating wirelessly (as indicated by an antenna in FIG. 2B) to, for example, a mobile health (mHealth) system, internet based healthcare (eHealth) services, and other healthcare systems that may monitor or use the measurements of the physiological parameter for clinical diagnosis or clinical research.

The information about the physiological parameter, initially acquired in vivo and provided by the transducer 134 (the first output signal) for signal processing, transmitted from inside the body by the first wireless system 142 (the second output signal), received outside the body, processed, and communicated by the second wireless system 212 (the third output signal) to the data communication system 222 of the computer system 220 and, finally extracted by circuitry in the data communication system 222, may be used by the processor 224 to obtain a measure of the physiological parameter.

Generally, the information extracted by the data communication system 222 would be an electrical waveform or a characteristic feature of an electrical waveform, for example, a maximum and a minimum value, an average value, or the like. In order to convert the electrical information to a measure of the physiological parameter, the processor 224 may need to execute coded instructions that include a calibration procedure using standardized measurements referred to as calibration data, as explained in further detail below.

The calibration data and the coded instructions which, when executed by the processor 224 results in a measure of the physiological parameter. The calibration data and the coded instructions may be stored in the memory 226 of the computer system 220. In some embodiment, the processor may obtain the measure of the physiological parameter in real time. In some other embodiment the information extracted by the data communication system 222 may be stored in memory 226 to be subsequently accessed by the processor 224. In some embodiments, the measure of the physiological parameter obtained by the processor 224 may be stored in the memory 226 and subsequently provided to the data communication system 222 to be communicated wirelessly to other information systems (e.g., mHealth or eHealth services).

The method for in vivo measurement of a physiological parameter using the sensor 100 (illustrated in FIGS. 1A-1C), and the measurement system 200, (illustrated in FIG. 2A and 2B) is explained using example embodiments suitable for measuring extravascular arterial BP.

Figure 3A:
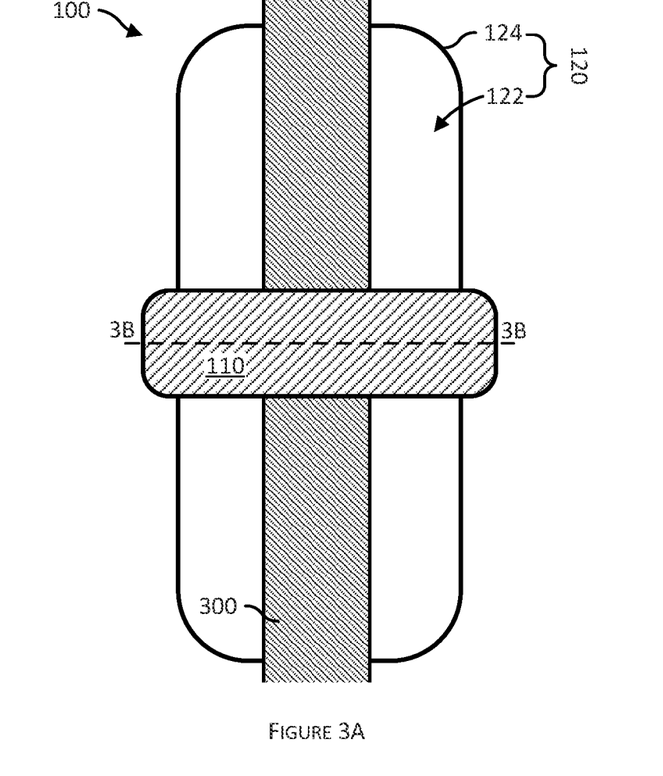
FIG. 3A illustrates a schematic of the sensor illustrated in FIG. 1A holding an artery.

FIG. 3A illustrates the sensor 100 holding an artery 300. For example, the sensor 100 may be implanted inside a human arm and configured to hold an artery (e.g., the brachial artery) between the clip no and the sheath 124 of the capsule 120. The capsule 120 may comprise glass and, in one embodiment, be shaped like a small rectangular prism having, for example, length and width dimensions of about 5 mm to about 15 mm and a depth of about 3 mm to about 5 mm. The clip no comprises a rigid material (e.g., Teflon) and may be about 1 mm to about 5 mm thick. The width of the clip 110 may be about 3 mm to about 10 mm. The curved shape of the clip no near the opening 130 helps to grip the artery 300 firmly and keep the sensor 100 in a suitable orientation relative to the artery even when there is internal motion caused by, for example, muscle movement. In some embodiment, the sensor 100 may be provided additional support by suturing the sensor to adjacent tissue when it is implanted inside the body.

Figure 3B:
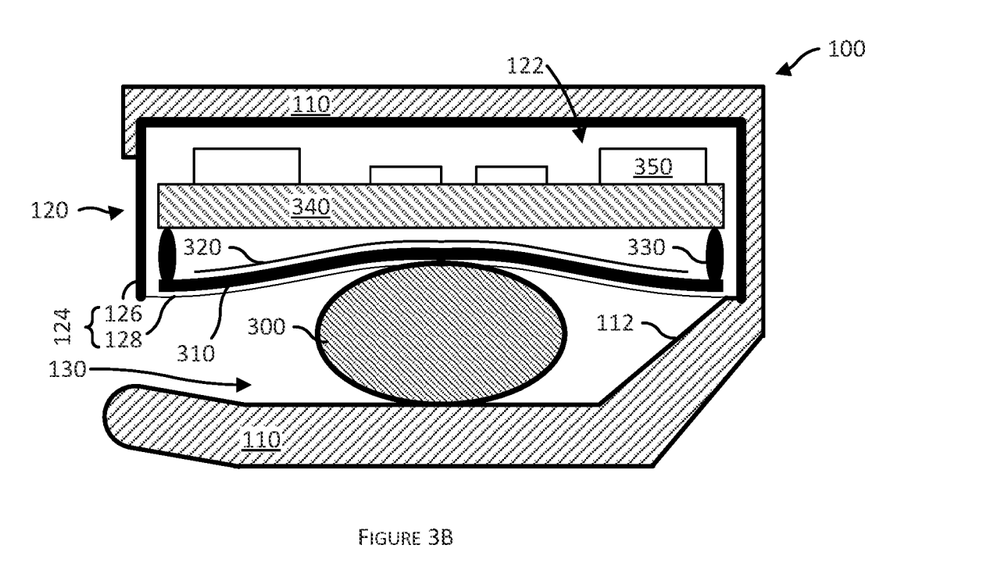
FIG. 3B illustrates a cross-sectional view of the sensor illustrated in FIG. 3A comprising a strain gauge.

A cross-sectional view, illustrated in FIG. 3B, shows the artery 300 positioned in the opening 130 between the inner surface 112 of the clip no and the second portion 128 of the sheath 124. The second portion 128 is flexible and, in various embodiments, may comprise glass thinned to a thickness of about 0.5 mm to about 0.3 mm, while the remaining first portion 126 of the sheath 124 may be comprising rigid glass about 1 mm to about 4 mm thick. The rigid first portion 126 provides support to the clip no as it wraps around the outside of the capsule 120. As illustrated in FIG. 3B, the second portion 128 is slightly bent as the inner surface 112 of the clip no holds the artery 300 firmly against the flexible second portion 128. The displacement of the flexible second portion 128 may be modulated by the artery 300 as it pulsates in response to the blood pressure oscillating between a high systolic pressure and a low diastolic pressure. In this embodiment, the time-varying displacement of the second portion 128 is used as the incoming signal indicative of the arterial BP (the physiological parameter for this example). A stronger incoming signal is obtained by positioning the artery 300 between a rigid and a flexible surface, as done in this example embodiment. Hence, a higher SNR may be achieved relative to positioning the artery between two flexible surfaces.

Still referring to FIG. 3B, a strain gauge 320, used as the pressure transducer in this example, is shown placed inside the cavity 122 attached to a flexible routing substrate 310, where the flexible routing substrate 310 is attached to a surface of the second portion 128 in the cavity 122. The flexible routing substrate 310 may comprise a conductive material such as copper embedded in a flexible matrix such as polyimide, and used to electrically connect the strain gauge 320 to connectors 330 comprising, for example, conductive epoxy. The connectors 330 connect the flexible routing substrate 310 to a printed circuit board (PCB) 340. The PCB is generally a flat laminated composite of metal lines embedded in an insulating matrix forming an interconnect network comprising, for example, copper clad laminates of prepreg (glass coated with resin). Various electronic components 350, such as those in electronic circuitry 140 described above with reference to FIG. 1C, may be attached to the PCB 340 and connected using an interconnect network in the PCB 340. In some embodiments, the metallization in the PCB may be configured to be an antenna.

Strain gauges are generally long, thin, temperature insensitive metal resistors comprising, for example, constantan, Karma alloy, or isoelastic alloy, attached to a flexible insulating carrier such as polyimide, epoxy, or glass-enforced epoxy. The resistance value changes with strain because of the geometrical changes in the wire length and cross-sectional area caused by strain. The resistance of the strain gauge 320 in FIG. 3B would thus respond to a change in the curvature of the flexible second portion 128 with a change in displacement resulting from the pulsations of the artery 300. In one embodiment, the strain gauge 320 may be connected to an electrical circuit such as a balanced Wheatstone bridge, where even a small change in the resistance of the strain gauge 320 can be detected as a change in an electrical signal, thereby generating an electrical signal indicative of the BP of the artery 300.

Pressure transducers based on other physical effects of strain may be used in other embodiments. For example, a piezoelectric material such as quartz and lead zirconate titanate (PZT) generates an electrical signal in response to strain. This property may be used to transduce the displacements of the second portion 128 to an electrical signal.

Figure 3C:
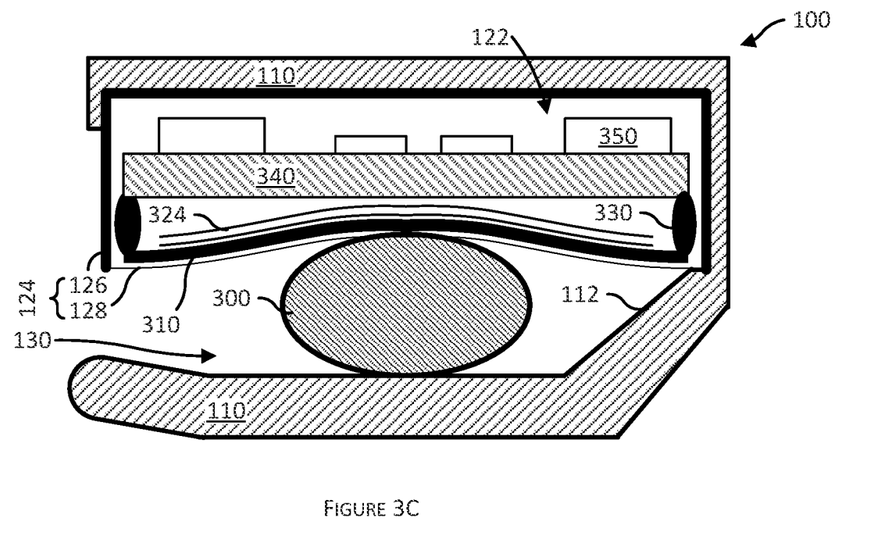
FIG. 3C illustrates a cross-sectional view of the sensor illustrated in FIG. 3A comprising a capacitor.

FIG. 3C illustrates an embodiment where the pressure transducer is a parallel plate capacitor 324 having a variable capacitance instead of the strain gauge 320 which has a variable resistance. The capacitance of parallel plate capacitors depend on the thickness of the capacitor dielectric. In a capacitor pressure transducer, the dielectric thickness, hence capacitance is varied by varying the distance separating the two plates. In one embodiment, the parallel plate capacitor 324 has one conductive plate that is a flexible diaphragm attached to the flexible routing substrate 310, as illustrated in FIG. 3C. The second plate may be rigid and electrically insulated from the flexible plate, for example attached to the PCB 340. The capacitor dielectric of the parallel plate capacitor 324 may be air. The pulsating artery 300 causes respective displacement of the flexible second portion 128 which, in turn, causes the flexible diaphragm to alter the dielectric thickness of the variable parallel plate capacitor 324. In one embodiment, the parallel plate capacitor 324 may be connected to be part of a resonator of an electrical oscillator. The resonance frequency would vary with the varying capacitance, thereby modulating the frequency of the output signal of the oscillator. The oscillation frequency may be detected to produce an electrical signal indicative of the BP of the artery 300.

Pressure transducers may use optical methods where the displacements of a flexible surface result in an optical response such as variations in an optical interference pattern produced using an interferometer or a deformable diffraction grating, or the variations in intensity of an optical image produced using a deformable mirror. An example embodiment of the sensor 100 using an optical pressure transducer (e.g., the deformable mirror) is illustrated in FIG. 3D.

Figure 3D:
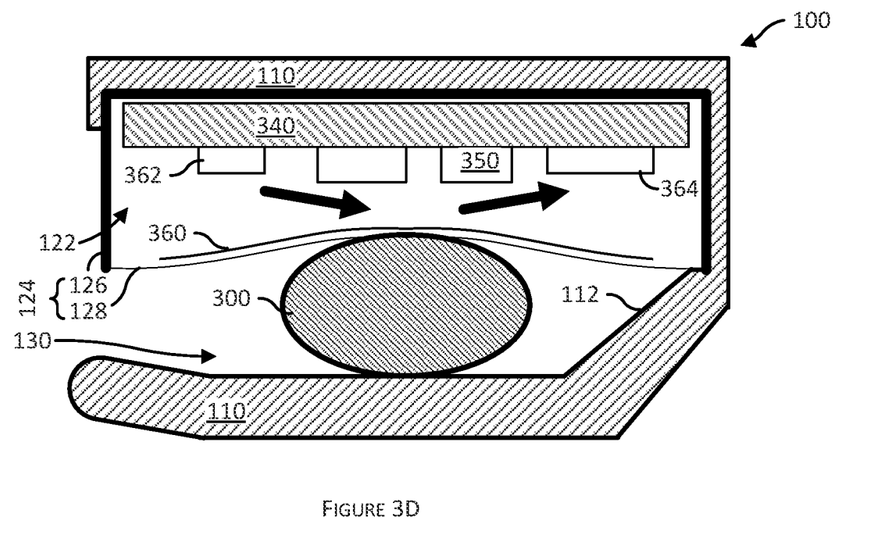
FIG. 3D illustrates a cross-sectional view of the sensor illustrated in FIG. 3A comprising a deformable mirror.

FIG. 3D illustrates an embodiment where the displacements of the second portion 128 of the sheath 124 are detected using a deformable mirror. In FIG. 3D, the deformable mirror 360 is a reflective metal coating in one embodiment, the mirror 360 being formed on a portion of the surface of the flexible second portion 128. A light source 362, for example, a light-emitting diode (LED) may be mounted on the PCB 340 at one side in the cavity 122 and a photodetector 364, for example, a photodiode may be mounted on the PCB 340 at an opposite side in the cavity 122. The light source 362 may be configured to illuminate the mirror 360, indicated by a downward pointing arrow in FIG. 3D. The photodetector 364 may be configured to receive the reflected light (indicated by an upward pointing arrow in FIG. 3D). In this arrangement, as illustrated in FIG. 3D, a deflection of the mirror 360 would alter the angle of the light being incident on the photodetector, thereby changing the intensity of the received light. In FIG. 3D, the mirror 360 is disposed over the flexible second portion 128. Accordingly, displacements of the flexible second portion 128 (caused by the pulsating artery 300) result in respective deflections of mirror 360. Thus, the electrical output of the photodetector 364 would be the first output signal, indicative of the arterial BP.

It is understood that, in various other embodiments, various other types of pressure transducers (e.g., detecting displacement using variation in tunneling current of a tunnel diode) may be used in a measurement system used for in vivo pressure measurement.

As described above with reference to FIGS. 3A-3D, in an arterial BP measurement method, the instantaneously varying BP in a pulsating artery may be converted in vivo by to an initial time-varying electrical signal (first output signal) by a transducer 134. The acquired information is subsequently provided to the processor 224 by the data communication system 222 of the computer system 220. As explained above, the pulsating artery held in vivo adjacent to the flexible second portion 128 of the sheath 124 causes vibrations that are detected by a transducer 134 of the sensor 100. The transducer 134 provides an electrical first output signal indicative of the arterial BP that is processed by various signal processing circuitry inside and outside the body. The information, initially acquired by the transducer 134, is extracted by the data communication system 222 from the third output signal, as described above. The conversion of this electrical data to arterial BP may be achieved by comparing with similar data that has been pre-calibrated against arterial BP obtained using a standardized method, for example, the auscultatory method of measuring systolic and diastolic blood pressures based on the Korotkoff sounds.

The conversion of the acquired electrical data to obtain a measure of arterial BP using the calibration data may be performed in the computer system 220 by the processor 224. The processor 224 may be configured to execute coded instructions which when executed results in a measure of the arterial BP. The coded instructions and the calibration data may be stored in memory 226 and accessed by the processor 224. The obtained measure of the arterial BP may be stored in memory 226 as a function of time or further processed to calculate the average BP per cycle or the mean arterial pressure (MAP).

The embodiments in this disclosure have been described in the context of measuring extravascular arterial blood pressure of a pulsating artery held by the sensor inside a living organism. A sensor small form factor may help reduce invasiveness of surgical procedure involved in implanting the sensor in the body. In various embodiments, the pulsating artery is held in contact with a flexible surface of a portion of the sensor. The regular repetitive deformation of the artery in response to its instantaneously changing blood pressure causes a time-varying displacement of the flexible surface which, in this example, may be the incoming signal indicative of a physiological parameter (e.g., blood pressure) of the biological sample. The incoming signal is converted to by a pressure transducer in the sensor. The blood pressure sensor may comprise one of various pressure transducers in various embodiments. The final measure of the BP may be obtained as an average value over a many pulses or as a function of time with a time discretization scale of a single pulse, thereby providing difficult to obtain information such as transient BP.

Example 1. A sensor including: a clip including an inner surface; a capsule including a cavity and a sheath enclosing the cavity, the sheath including a first portion attached to the inner surface and a second portion, the capsule and the clip being configured to hold in vivo an object within an opening between the second portion of the capsule and the inner surface of the clip; a transducer disposed in the cavity, the transducer being configured to detect in vivo an incoming signal received via the second portion, the incoming signal indicative of a physiological parameter of the object inside a living organism; and electronic circuitry disposed in the cavity and coupled to the transducer, where the electronic circuitry includes a wireless system, the wireless system including a power supply system, the power supply system configured to receive power wirelessly from an external radio frequency (RF) power source and supply power to operate the electronic circuitry, the external RF power source configured to be outside the living organism, and where the electronic circuitry is configured to transmit a signal containing information about the physiological parameter obtained from the incoming signal.

Example 2. The sensor of example 1, where the object is part of a human artery.

Example 3. The sensor of one of examples 1 or 2, where the sheath includes glass.

Example 4. The sensor of one of examples 1 to 3, where the first portion includes a rigid material and the second portion includes a flexible material; and where the incoming signal is a displacement of the second portion.

Example 5. The sensor of one of examples 1 to 4, where the information about the physiological parameter includes information on pressure within the biological sample, and where the transducer includes a strain gauge, a piezoelectric device, a piezoresistive device, a variable capacitive device, a variable inductive device, a deformable mirror, a deformable diffraction grating, an interferometer, or a quantum tunneling device.

Example 6. The sensor of one of examples 1 to 5, where the transducer includes a capacitor, where a first plate of the capacitor is attached to the second portion of the capsule and the second plate of the capacitor is attached to a structure fixed within the capsule.

Example 7. The sensor of one of examples 1 to 6, further including: a flexible routing substrate attached to the second portion of the capsule; and connectors coupling the flexible routing substrate to a printed circuit board supporting the electronic circuitry, the transducer including a strain gauge that is attached to the flexible routing substrate.

Example 8. The sensor of one of examples 1 to 7, further including: a deformable mirror attached to the second portion of the capsule; a light source disposed on a printed circuit board, the light source configured to emit light towards the mirror; and a photodetector disposed on the printed circuit board, the photodetector configured to detect light reflected from the mirror.

Example 9. The sensor of one of examples 1 to 8, where the transducer includes a chemical sensor device, a pH sensor device, a thermometer, a thermoelectric device, an ultrasound detector, a Hall effect sensor, an electric potential detector, an x-ray detector, a photodetector, or a radioactive radiation detector.

Example 10. The sensor of one of examples 1 to 9, where the transducer includes an outer surface that is part of the second portion.

Example 11. The sensor of one of examples 1 to 10, where the transducer is sealed from the opening by the second portion.

Example 12. A measurement system including: a sensor configured to be attached within a living organism, the sensor including: a capsule including a cavity and a sheath enclosing the cavity, the sheath including a first portion and a second portion; a clip disposed outside the capsule, the clip being configured to attach to the first portion and to hold in vivo an object between the second portion and the clip; a transducer disposed in the cavity, the transducer being configured to detect in vivo an incoming signal received via the second portion, the incoming signal indicative of a physiological parameter of the object; and electronic circuitry disposed in the cavity and coupled to the transducer, where the electronic circuitry includes a first wireless system, the first wireless system including a power supply system configured to receive power wirelessly from an external radio frequency (RF) power source and supply power to operate the electronic circuitry, the external RF power source configured to be outside the living organism, and where the electronic circuitry is configured to transmit a signal containing information about the physiological parameter obtained from the incoming signal; and an electronic system configured to be outside the living organism, the electronic system including: a second wireless system, the second wireless system being configured to communicate wirelessly with the first wireless system; and a computer system.

Example 13. The measurement system of example 12, where the computer system includes: a data communication system, the data communication system configured to communicate with the second wireless system; a processor configured to execute coded instructions; and a memory, where the memory has stored calibration data and coded instructions which when executed results in a measure of the physiological parameter.

Example 14. The measurement system of one of examples 12 or 13, where the computer system is included in a mobile system.

Example 15. The measurement system of one of examples 12 to 14, where the computer system is included in a smart phone.

Example 16. The measurement system of one of examples 12 to 15, where the electronic circuitry disposed in the cavity further includes a programmable device.

Example 17. The measurement system of one of examples 12 to 16, where the electronic circuitry disposed in the cavity further includes: an analog to digital (A/D) converter; and a digital signal processor coupled to the digital output of the A/D converter.

Example 18. The measurement system of one of examples 12 to 17, where the computer system and the second wireless system are configured to communicate wirelessly with each other.

Example 19. The measurement system of one of examples 12 to 18, where the second wireless system is a mobile system configured to be wearable.

Example 20. The measurement system of one of examples 12 to 19, where the computer system and the second wireless system are configured to communicate via a wired connection.

Example 21. The measurement system of one of examples 12 to 20, where the second wireless system includes the external radio frequency power source.

Example 22. The measurement system of one of examples 12 to 21, where the power supply system further includes a rechargeable battery.

Example 23. A measurement method, where the method provides a measure of a physiological parameter of an object inside a living organism, the method including: implanting a sensor inside the living organism, the sensor including: a capsule including a cavity and a sheath enclosing the cavity, the sheath including a first portion and a second portion; a clip disposed outside the capsule; a transducer disposed in the cavity, the transducer being configured to detect an incoming signal from the object received via the second portion; and electronic circuitry disposed in the cavity and coupled to the transducer, the electronic circuitry including a first wireless system; configuring the clip to attach to the first portion and to hold in vivo the object between the second portion and the clip; converting the incoming signal in vivo to a first output signal with the transducer, the first output signal being an electrical signal indicative of the physiological parameter of the biological sample; generating a second output signal from the first output signal with the electronic circuitry, the second output signal containing information about the physiological parameter; transmitting the second output signal wirelessly to an electronic system disposed outside the living organism with the first wireless system; and obtaining a measure of the physiological parameter from the second output signal with the electronic system.

Example 24. The measurement method of example 23, where the electronic system includes: a second wireless system; and a computer system, the computer system including: a data communication system, the data communication system configured to communicate with the second wireless system; a processor configured to execute coded instructions; and a memory, where the memory has stored calibration data and coded instructions which when executed results in a measure of the physiological parameter.

Example 25. The measurement method of one of examples 23 or 24, where obtaining a measure of the physiological parameter from the second output signal includes: configuring the second wireless system to receive wirelessly the second output signal transmitted from the first wireless system; generating a third output signal from the second output signal with the second wireless system, the third output signal containing information about the physiological parameter; transmitting the third output signal to the data communication system of the computer system with the second wireless system; obtaining a measure of the physiological parameter from the third output signal with the computer system, the obtaining including: extracting the information about the physiological parameter from the third output signal; computing a measure of the physiological parameter by executing the coded instructions with the processor using the calibration data and the extracted information about the physiological parameter; and storing the measure of the physiological parameter in a memory of the computer system.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A sensor comprising:
a clip comprising an inner surface;
a capsule comprising a cavity and a sheath comprising a first portion and a second portion together enclosing the cavity,
wherein the sheath is made of a single electrically insulating material,
wherein the first portion is attached to the inner surface, the first portion comprises a first thickness, and is configured to be a rigid outer surface of the sensor,
wherein the second portion comprises a second thickness less than the first thickness and is configured to be a flexible outer surface of the sensor, and
wherein the capsule and the clip are configured to hold in vivo a tubular object of a living organism within an opening between the second portion of the sheath and the inner surface of the clip through direct contact of the tubular object both with the inner surface and with the second portion of the sheath to hold the tubular object firmly against the flexible outer surface of the sensor so that the second portion is bent by the tubular object;
wherein the opening between the second portion of the sheath and the inner surface of the clip is defined by a single projection of the clip, the single projection comprising a proximal end attached to the capsule and a distal end comprising a curved shape,
a transducer disposed in the cavity, the transducer being configured to detect in vivo an incoming signal received via the second portion, the incoming signal being a displacement of the second portion and indicative of a physiological parameter of the tubular object inside the living organism; and electronic circuitry disposed in the cavity and coupled to the transducer,
wherein the electronic circuitry comprises a wireless system, the wireless system comprising a power supply system, the power supply system configured to receive power wirelessly from an external radio frequency (RF) power source and supply power to operate the electronic circuitry, the external RF power source configured to be outside the living organism, and wherein the electronic circuitry is configured to transmit a signal containing information about the physiological parameter obtained from the incoming signal.

2. The sensor of claim 1, wherein the power supply system further comprises a rechargeable battery.

3. The sensor of claim 1, wherein the tubular object is a human artery.

4. The sensor of claim 1, wherein the single electrically insulating material is glass.

5. The sensor of claim 1, wherein the information about the physiological parameter comprises information on pressure within a biological sample, and wherein the transducer comprises a strain gauge, a piezoelectric device, a piezoresistive device, a variable capacitive device, a variable inductive device, a deformable mirror, a deformable diffraction grating, an interferometer, or a quantum tunneling device.

6. The sensor of claim 1, wherein the transducer comprises a capacitor, wherein a first plate of the capacitor is attached to the second portion of the sheath and a second plate of the capacitor is attached to a structure fixed within the capsule.

7. The sensor of claim 1, further comprising:
a flexible routing substrate attached to the second portion of the sheath; and
connectors coupling the flexible routing substrate to a printed circuit board supporting the electronic circuitry, the transducer comprising a strain gauge that is attached to the flexible routing substrate.

8. The sensor of claim 1, further comprising:
a deformable mirror attached to the second portion of the sheath;
a light source disposed on a printed circuit board, the light source configured to emit light towards the deformable mirror; and
a photodetector disposed on the printed circuit board, the photodetector configured to detect light reflected from the deformable mirror.

9. The sensor of claim 1, wherein the transducer comprises a chemical sensor device, a pH sensor device, a thermometer, a thermoelectric device, an ultrasound detector, a Hall effect sensor, an electric potential detector, an x-ray detector, a photodetector, or a radioactive radiation detector.

10. A measurement system comprising:
a sensor configured to be attached within a living organism, the sensor comprising:
a capsule comprising a cavity and a sheath comprising a first portion and a second portion together enclosing the cavity,
wherein the sheath is made of a single electrically insulating material,
wherein the first portion comprises a first thickness and is configured to be a rigid outer surface of the sensor, and
wherein the second portion comprises a second thickness less than the first thickness and is configured to be a flexible outer surface of the sensor;
a clip disposed outside the capsule, the clip being configured to attach to the first portion and to hold in vivo a tubular object of the living organism between the second portion and the clip through direct contact of the tubular object both with the clip and with the second portion of the sheath to hold the tubular object firmly against the flexible outer surface of the sensor so that the second portion is bent by the tubular object;
wherein an opening between the second portion of the sheath and the inner surface of the clip is defined by a single projection of the clip, the single projection comprising a proximal end attached to the capsule and a distal end comprising a curved shape,
a transducer disposed in the cavity, the transducer being configured to detect in vivo an incoming signal received via the second portion, the incoming signal indicative of a physiological parameter of the tubular object; and
electronic circuitry disposed in the cavity and coupled to the transducer,
wherein the electronic circuitry comprises a first wireless system, the first wireless system comprising a power supply system configured to receive power wirelessly from an external radio frequency (RF) power source and supply power to operate the electronic circuitry, the external RF power source configured to be outside the living organism, and
wherein the electronic circuitry is configured to transmit a signal containing information about the physiological parameter obtained from the incoming signal; and
an electronic system configured to be outside the living organism, the electronic system comprising:
a second wireless system, the second wireless system being configured to communicate wirelessly with the first wireless system; and
a computer system.

11. The measurement system of claim 10, wherein the computer system comprises:
a data communication system, the data communication system configured to communicate with the second wireless system;
a processor configured to execute coded instructions; and
a memory, wherein the memory has stored calibration data and coded instructions which when executed results in a measure of the physiological parameter.

12. The measurement system of claim 10, wherein the electronic circuitry disposed in the cavity further comprises a programmable device.

13. The measurement system of claim 10, wherein the second wireless system is a mobile system configured to be wearable.

14. The measurement system of claim 10, wherein the second wireless system comprises the external RF power source.

15. A measurement method for measuring a physiological parameter of a tubular object inside a living organism, the method comprising:
implanting a sensor inside the living organism, the sensor comprising:
a capsule comprising a cavity and a sheath comprising a first portion and a second portion together enclosing the cavity,
wherein the sheath is made of a single electrically insulating material,
wherein the first portion comprises a first thickness and is configured to be a rigid outer surface of the sensor, and
wherein the second portion comprises a second thickness less than the first thickness and is configured to be a flexible outer surface of the sensor;
a clip disposed outside the capsule;
a transducer disposed in the cavity, the transducer being configured to detect an incoming signal from the tubular object received via the second portion; and
electronic circuitry disposed in the cavity and coupled to the transducer, the electronic circuitry comprising a first wireless system;
configuring the clip to attach to the first portion and to hold in vivo the tubular object between the second portion and the clip through direct contact of the tubular object both with the clip and with the second portion of the sheath to hold the tubular object firmly against the flexible outer surface of the sensor so that the second portion is bent by the tubular object;

wherein an opening between the second portion of the sheath and the inner surface of the clip is defined by a single projection of the clip, the single projection comprising a proximal end attached to the capsule and a distal end comprising a curved shape, converting the incoming signal in vivo to a first output signal with the transducer, the first output signal being an electrical signal indicative of the physiological parameter of the tubular object inside the living organism;

generating a second output signal from the first output signal with the electronic circuitry, the second output signal containing information about the physiological parameter;

transmitting the second output signal wirelessly to an electronic system disposed outside the living organism with the first wireless system; and obtaining a measure of the physiological parameter from the second output signal with the electronic system.

16. The measurement method of claim 15, wherein the electronic system comprises:
a second wireless system; and
a computer system, the computer system comprising:
  a data communication system, the data communication system configured to communicate with the second wireless system;
  a processor configured to execute coded instructions; and
  a memory, wherein the memory has stored calibration data and coded instructions which when executed results in the electronic system obtaining the measure of the physiological parameter.

17. The measurement method of claim 16, wherein obtaining the measure of the physiological parameter from the second output signal comprises:
  configuring the second wireless system to receive wirelessly the second output signal transmitted from the first wireless system;
  generating a third output signal from the second output signal with the second wireless system, the third output signal containing the information about the physiological parameter;
  transmitting the third output signal to the data communication system of the computer system with the second wireless system;
  obtaining the measure of the physiological parameter from the third output signal with the computer system, the obtaining comprising:
    extracting the information about the physiological parameter from the third output signal;
    computing the measure of the physiological parameter by executing the coded instructions with the processor using the calibration data and the extracted information about the physiological parameter; and
    storing the measure of the physiological parameter in the memory of the computer system.

18. The sensor of claim 1, wherein the second portion is a thinned portion integral with the first portion.

19. The sensor of claim 1, wherein the capsule is shaped like a rectangular prism comprising a capsule length dimension and a capsule width dimension both between about 5 mm and about 15 mm and a capsule depth dimension between about 3 mm to about 5 mm, and wherein the clip comprises a clip width dimension less than the capsule length dimension, the clip width dimension being between about 3 mm and about 10 mm.

* * * * *

UNITED STATES PATENT AND TRADEMARK OFFICE
CERTIFICATE OF CORRECTION

PATENT NO. : 12,011,252 B2
APPLICATION NO. : 17/233776
DATED : June 18, 2024
INVENTOR(S) : Rahul Saini et al.

It is certified that error appears in the above-identified patent and that said Letters Patent is hereby corrected as shown below:

In the Claims

In Column 15, Line 66, Claim 10:
Change "sheath and the inner surface of the clip is defined"
To --sheath and an inner surface of the clip is defined--

In Column 17, Line 7, Claim 15:
Change "sheath and the inner surface of the clip is defined"
To --sheath and an inner surface of the clip is defined--

Signed and Sealed this
Fifteenth Day of April, 2025

Coke Morgan Stewart
*Acting Director of the United States Patent and Trademark Office*